US00PP26968P2

(12) United States Plant Patent
Pieters et al.

(10) Patent No.: US PP26,968 P2
(45) Date of Patent: Jul. 19, 2016

(54) ***GUZMANIA* PLANT NAMED 'FLO'**

(50) Latin Name: ***Guzmania cardinalis*×*Guzmania wittmackii***
Varietal Denomination: Flo

(71) Applicants: Luc Pieters, Laarne (BE); Caroline De Meyer, Laarne (BE)

(72) Inventors: Luc Pieters, Laarne (BE); Caroline De Meyer, Laarne (BE)

( * ) Notice: Subject to any disclaimer, the term of this patent is extended or adjusted under 35 U.S.C. 154(b) by 83 days.

(21) Appl. No.: 14/121,560

(22) Filed: Sep. 17, 2014

(51) Int. Cl.
*A01H 5/00* (2006.01)

(52) U.S. Cl.
USPC ..... Plt./371

(58) Field of Classification Search
USPC ..... Plt./371
See application file for complete search history.

*Primary Examiner* — Annette Para
(74) *Attorney, Agent, or Firm* — C. A. Whealy

(57) ABSTRACT

A new and distinct cultivar of *Guzmania* plant named 'Flo', characterized by its upright and outwardly arching growth habit; narrow dark green-colored leaves; large inflorescences with showy dark red-colored bracts; and good postproduction longevity.

2 Drawing Sheets

Botanical designation: *Guzmania cardinalis*×*Guzmania wittmackii.*

Cultivar denomination: 'FLO'.

BACKGROUND OF THE INVENTION

The present invention relates to a new and distinct cultivar of *Guzmania* plant, botanically known as *Guzmania cardinalis*×*Guzmania wittmackii* and hereinafter referred to by the name 'Flo'.

The new *Guzmania* plant is a product of a planned breeding program conducted by the Inventors in Laarne, Belgium. The objective of the breeding program is to create new *Guzmania* plants having unique bract colors and enhanced postproduction longevity.

The new *Guzmania* originated from a cross-pollination made by the Inventors in January, 2009 in Laarne, Belgium of an unnamed proprietary selection of *Guzmania cardinalis*, not patented, as the female, or seed, parent with an unnamed proprietary selection of *Guzmania wittmackii*, not patented, as the male, or pollen, parent. The new *Guzmania* plant was discovered and selected by the Inventors as a single flowering plant from within the progeny of the stated cross-pollination in a controlled environment in Laarne, Belgium in January, 2011.

Asexual reproduction of the new *Guzmania* plant by tissue culture in a controlled environment in Laarne, Belgium since June, 2012 has shown that the unique features of this new *Guzmania* plant are stable and reproduced true to type in successive generations.

SUMMARY OF THE INVENTION

Plants of the new *Guzmania* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Flo'. These characteristics in combination distinguish 'Flo' as a new and distinct *Guzmania* plant:

1. Upright and outwardly arching growth habit.
2. Narrow dark green-colored leaves.
3. Large inflorescences with showy dark red-colored bracts.
4. Good postproduction longevity.

Plants of the new *Guzmania* can be compared to plants of the female parent selection. Plants of the new *Guzmania* differ primarily from plants of the female parent selection in the following characteristics:

1. Plants of the new *Guzmania* are taller and more vigorous than plants of the female parent selection.
2. Plants of the new *Guzmania* have darker red-colored bracts than plants of the female parent selection.

Plants of the new *Guzmania* can be compared to plants of the male parent selection. Plants of the new *Guzmania* differ primarily from plants of the male parent selection in bract color as plants of the male parent selection have orange-colored bracts.

Plants of the new *Guzmania* can be compared to plants of *Guzmania* 'Indian Night', not patented. In side-by-side comparisons conducted in Laarne, Belgium, plants of the new *Guzmania* and 'Indian Night' differed in the following characteristics:

1. Plants of the new *Guzmania* and 'Indian Night' differed in bract color as plants of 'Indian Night' had purple-colored bracts.
2. Bracts of plants of the new *Guzmania* were strongly curved whereas bracts of plants of 'Indian Night' were moderately curved.

BRIEF DESCRIPTION OF THE PHOTOGRAPHS

The accompanying colored photographs illustrate the overall appearance of the new *Guzmania* plant showing the colors as true as it is reasonably possible to obtain in colored reproductions of this type. Colors in the photographs may differ slightly from the color values cited in the detailed botanical description which accurately describe the colors of the new *Guzmania* plant.

The photograph on the first sheet comprises a side perspective view of a typical flowering plant of 'Flo' grown in a container.

The photograph on the second sheet is a close-up view of a typical flowering plant of 'Flo'.

DETAILED BOTANICAL DESCRIPTION

The aforementioned photographs and following observations, measurements and values describe plants grown during the late spring and early summer in 13-cm containers in a glass-covered greenhouse in Laarne, Belgium and under cultural practices typical of commercial *Guzmania* production. During the production of the plants, day temperatures ranged from 21° C. to 30° C., night temperatures ranged from 20° C. to 21° C. and maximum light levels were 18,000 lux. Plants were three years old when the photographs and description were taken. In the following description, color references are made to The Royal Horticultural Society Colour Chart, 2007 Edition, except where general terms of ordinary dictionary significance are used.

Botanical classification: *Guzmania cardinalis*×*Guzmania wittmackii* 'Flo'.

Parentage:

*Female, or seed, parent*.—Unnamed proprietary selection of *Guzmania cardinalis*, not patented.

*Male, or pollen, parent*.—Unnamed proprietary selection of *Guzmania wittmackii*, not patented.

Propagation:

*Type*.—By tissue culture.

*Root description*.—Thick, fleshy; creamy white in color.

*Rooting habit*.—Medium density.

Plant description:

*Plant and growth habit*.—Upright and outwardly arching plant habit; broad inverted triangle; basal rosette of outwardly curved strap-like leaves affixed in tight spiral ranks; terminal inflorescence on an upright scape emerging from the center of the basal rosette; moderately vigorous to vigorous growth habit.

*Plant height, soil surface to top of inflorescence*.—About 57.2 cm.

*Plant diameter or spread*.—About 70.3 cm.

Leaf description:

*Arrangement*.—Basal rosette, spiral phyllotaxis; leaves sessile.

*Quantity of leaves per plant*.—Plants typically produce about 18 leaves prior to inflorescence development.

*Length*.—About 40.8 cm.

*Width*.—About 4.8 cm.

*Shape*.—Ligulate.

*Apex*.—Apiculate; twisting.

*Margin*.—Entire.

*Aspect*.—Leaves curved outward over their length and arching downward towards the apex.

*Texture, upper and lower surfaces*.—Leathery, stiff; smooth, glabrous.

*Venation*.—Parallel.

*Color*.—Developing leaves, upper surface: Slightly darker than between 137A and 146A. Developing leaves, lower surface: Between 137B to 137C and 143A. Fully expanded leaves, upper surface: Close to N137A; venation, close to N137A. Fully expanded leaves, lower surface: Between 146A and 147A; venation, close to between 146A and 147A.

Inflorescence description:

*Inflorescence form*.—Spike inflorescence form originating inside the leaf rosette; about 14 flowers develop per inflorescence; flowers sessile.

*Time to flower*.—Plants begin flowering about ten months after planting; plants flower naturally during late winter into the spring in Belgium.

*Flower longevity*.—Individual flowers last about six weeks on the plant; flowers persistent.

*Fragrance*.—None detected.

*Inflorescence length*.—About 19.4 cm.

*Inflorescence diameter*.—About 21 cm.

*Flower buds*.—Length: About 6.1 cm. Diameter: About 1.6 cm. Shape: Lanceolate. Color: Close to 34B to 34C; towards the base, close to 160B.

*Flowers*.—Length: About 6.6 cm. Diameter: About 1.8 cm. Shape: Lanceolate.

*Petals*.—Quantity per flower: Six. Length: About 3.2 cm. Width: About 3.5 mm. Shape: Narrowly lanceolate. Apex: Acute. Base: Truncate. Margin: Entire. Texture, upper and lower surfaces: Smooth, glabrous. Color: When opening, upper and lower surfaces: Close to 5B. Fully opened, upper and lower surfaces: Close to 158C to 158D.

*Lower (scape) bracts*.—Quantity per flower: One. Length: About 17.5 cm. Width: About 4.2 cm. Shape: Ligulate; curved downward. Apex: Acute. Base: Sheathing. Margin: Entire. Texture: Smooth, glabrous. Color, upper surface: Close to 45A; apex, close to N137A; sheath, close to 144A. Color, lower surface: Close to 45A; apex, close to 137B; sheath, close to 144A.

*Upper bracts*.—Quantity per flower: One. Length: About 13.5 cm. Width: About 3.8 cm. Shape: Ligulate; curved downward. Apex: Acute. Base: Sheathing. Margin: Entire. Texture: Smooth, glabrous. Color, upper and lower surfaces: Close to 42A; apex, close to 45A; sheath, close to 144A.

*Sepals*.—Quantity per flower: Three in a single whorl. Length: About 5.7 cm. Width: About 5 mm. Shape: Narrowly lanceolate. Apex: Acuminate. Base: Obtuse to broadly acute. Margin: Entire. Texture, upper and lower surfaces: Smooth, glabrous. Color, upper and lower surfaces: Close to 34B to 34C; towards the base, close to 151D.

*Scapes*.—Length: About 45.4 cm. Diameter: About 1 cm. Strength: Strong. Aspect: Typically erect. Texture: Smooth, glabrous. Color: Close to between 145C and 150C.

*Stamens*.—Quantity per flower: About twelve. Filament length: About 3.7 cm. Filament color: Close to 152D. Anther shape: Lanceolate. Anther length: About 1 cm. Anther color: Close to 150D. Pollen amount: None observed.

*Pistils*.—Quantity per flower: One. Pistil length: About 4.5 cm. Stigma shape: Three-lobed. Stigma color: Close to 151A. Style length: About 3.7 cm. Style color: Close to 150D. Ovary color: Close to 157B to 157D.

*Fruits and seeds*.—Fruit and seed production have not been observed on plants of the new *Guzmania*.

Temperature tolerance: Plants of the new *Guzmania* have been observed to tolerate high temperatures about 40° C. and to be hardy to USDA Hardiness Zone 10.

Interiorscape performance: Plants of the new *Guzmania* have been observed to have good postproduction longevity under interior conditions.

Disease & pest resistance: Resistance to pathogens and pests common to *Guzmania* plants has not been observed.

It is claimed:

1. A new and distinct *Guzmania* plant named 'Flo' as illustrated and described.

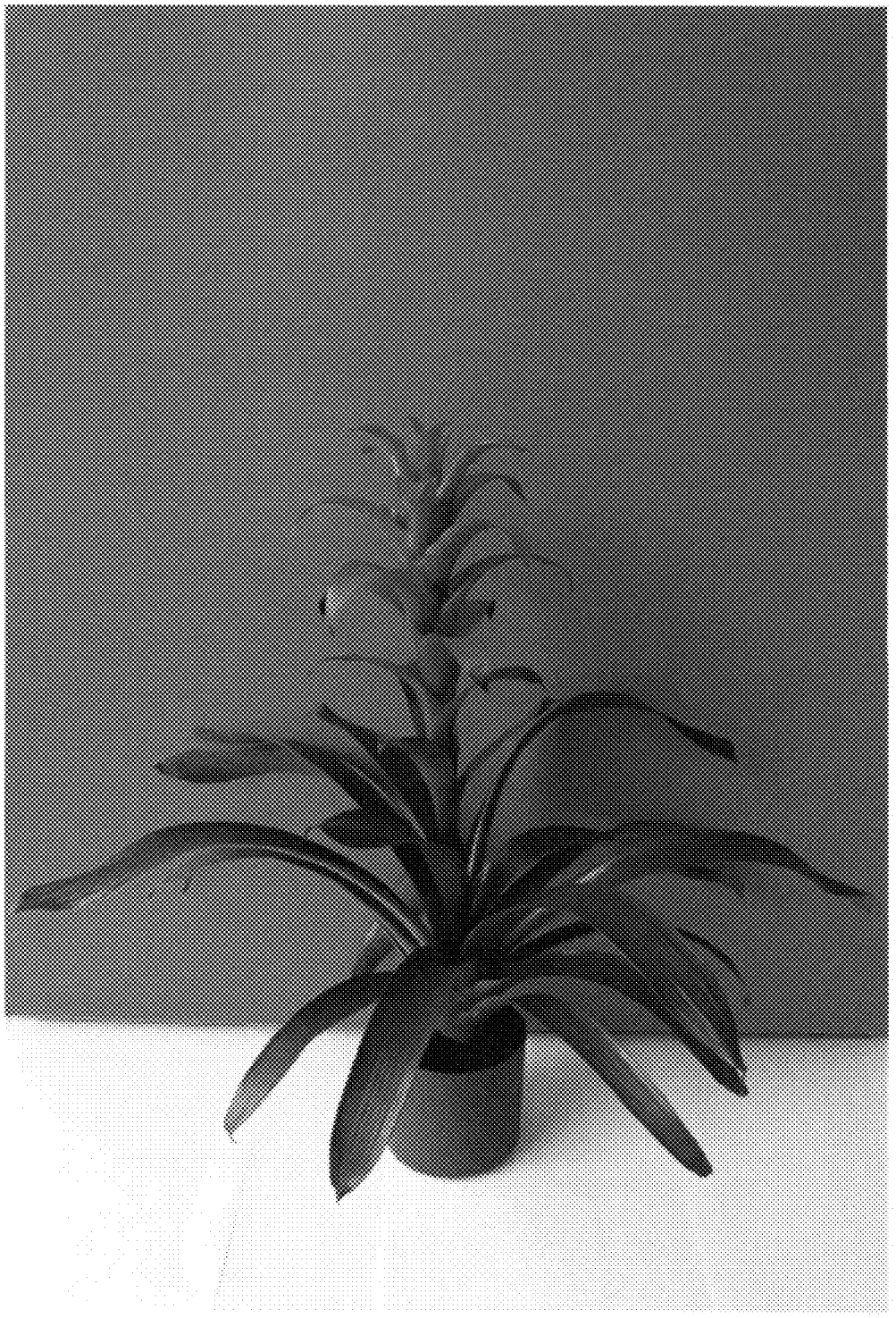

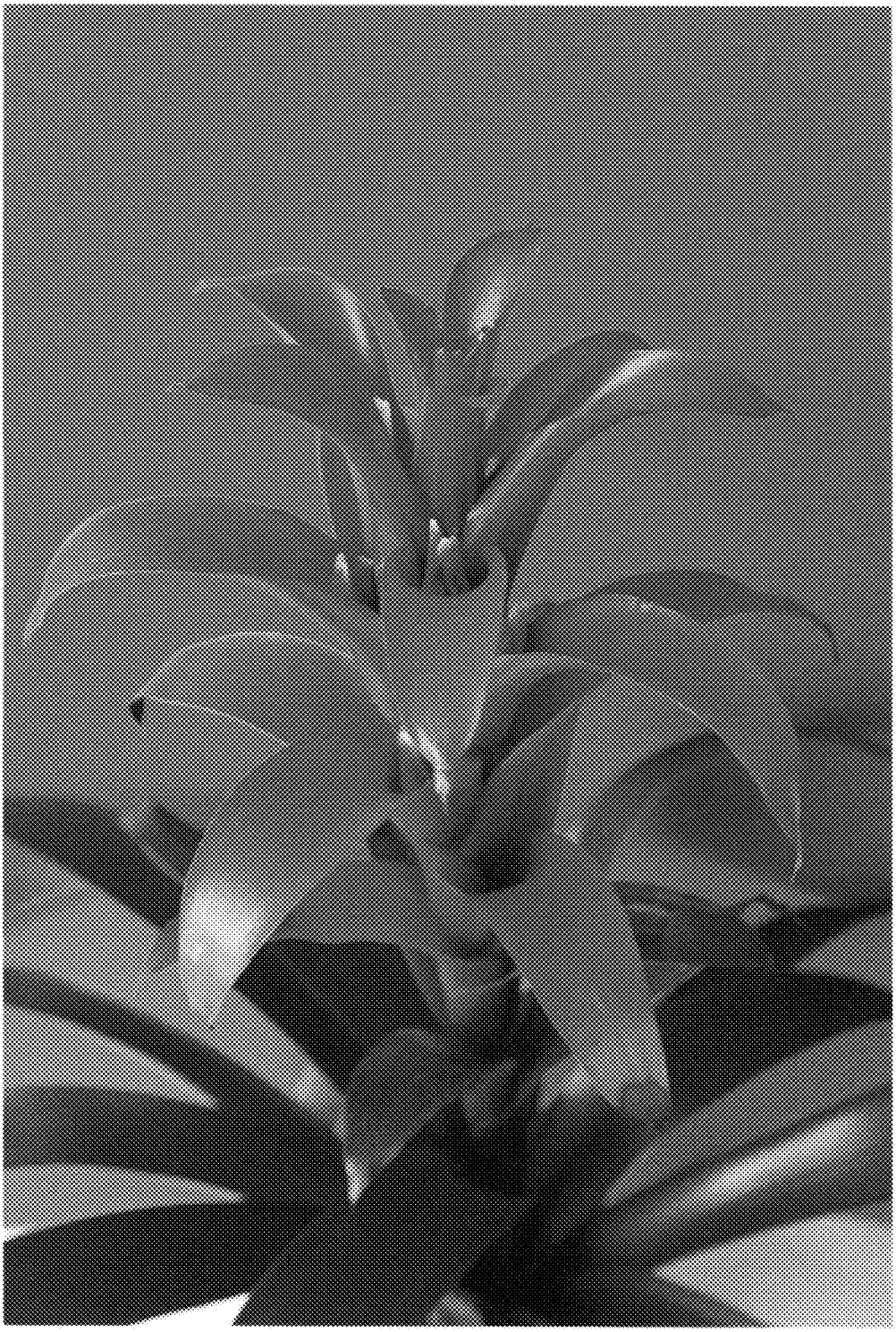

* * * * *